United States Patent [19]
Guerry et al.

[11] Patent Number: 5,177,067
[45] Date of Patent: Jan. 5, 1993

[54] SUBSTITUTED AMINOALKYL BIPHENYL COMPOUNDS AND METHOD OF TREATING FUNGAL INFECTIONS

[75] Inventors: Philippe Guerry, Basel; Synèse Jolidon, Birsfelden, both of Switzerland

[73] Assignee: Hoffmann-LaRoche Inc., Nutley, N.J.

[21] Appl. No.: 718,495

[22] Filed: Jun. 19, 1991

[30] Foreign Application Priority Data

Jun. 29, 1990 [CH] Switzerland .................. 2177/90
Mar. 27, 1991 [CH] Switzerland .................... 942/91

[51] Int. Cl.[5] .................... A61K 31/135; C07C 211/27
[52] U.S. Cl. .................... 514/183; 514/210; 514/468; 514/524; 514/648; 514/650; 548/578; 548/950; 548/967; 548/968; 558/415; 564/323; 564/337
[58] Field of Search .......... 564/323, 337; 558/415; 548/578, 950, 967, 968; 514/183, 210, 468, 524, 648, 650

[56] References Cited

U.S. PATENT DOCUMENTS 4,939,148  7/1990  Stutz et al. ............... 514/649
5,041,669  8/1991  Tafesh et al. ............... 564/337

FOREIGN PATENT DOCUMENTS 2185980  8/1987  United Kingdom .

*Primary Examiner*—Richard L. Raymond
*Attorney, Agent, or Firm*—George M. Gould; George W. Johnson; Stephen L. Malaska

[57] ABSTRACT

Antimycotically-active compounds of the formula

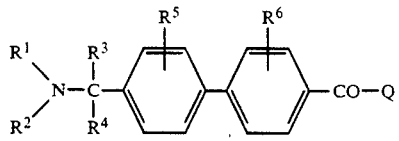

wherein $R^1$ and $R^2$ each independently are hydrogen, $C_{1-7}$-alkyl or $C_{2-7}$-alkenyl or together are a straight chain $C_{2-4}$-alkylene; $R^3$ and $R^4$ each independently are hydrogen or $C_{1-7}$-alkyl; $R^5$ and $R^6$ each independently are hydrogen, halogen, trifluoromethyl, nitro, cyano, $C_{1-7}$-alkoxy or $C_{1-7}$-alkyl; and Q is an unsubstituted or substituted phenyl or naphthyl group, wherein the substituents are at least one of halogen, trifluoromethyl, cyano, nitro, $C_{1-7}$-alkyl, $C_{1-7}$-alkoxy; $C_{2-10}$-alkenyl; or a substituted or unsubstituted $C_{1-10}$-alkyl group wherein said substituents are at least one hydroxy group; and pharmaceutically acceptable acid addition salts thereof.

11 Claims, No Drawings

SUBSTITUTED AMINOALKYL BIPHENYL COMPOUNDS AND METHOD OF TREATING FUNGAL INFECTIONS

BACKGROUND

This invention relates to certain substituted aminoalkyl biphenyl compounds having antimycotic activity and which exhibit synergistic effects in combination with known antimycotically-active compounds such as ketoconazole and terbinafine, compounds which inhibit biosynthesis of certain sterols. The invention also relates to pharmaceutical compositions, methods of antimycotic treatment and methods of preparation.

SUMMARY

The present invention is concerned with compounds of the general formula

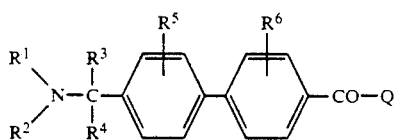

wherein $R^1$ and $R^2$ each independently are hydrogen, $C_{1-7}$-alkyl or $C_{2-7}$-alkenyl, or together are a straight chain $C_{2-4}$-alkylene; $R^3$ and $R^4$ each independently are hydrogen or $C_{1-7}$-alkyl; $R^5$ and $R^6$ each independently are hydrogen, halogen, trifluoromethyl, nitro, cyano, $C_{1-7}$-alkoxy or $C_{1-7}$-alkyl; and Q is an unsubstituted or substituted phenyl or naphthyl group, wherein the substituents are at least one of halogen, trifluoromethyl, cyano, nitro, $C_{1-7}$-alkyl, $C_{1-7}$-alkoxy; $C_{2-10}$-alkenyl; or a substituted or unsubstituted $C_{1-10}$-alkyl group wherein said substituents are at least one hydroxy group; or
pharmaceutically acceptable acid addition salts thereof.

The compounds of this invention have valuable pharmacological properties. In particular, they have a pronounced antimycotic activity and exhibit synergistic effects in combination with known antimycotically-active substances such as ketoconazole and terbinafine which inhibit biosynthesis of certain sterols. The compounds of formula I can accordingly be used as medicaments, especially for the control or prevention of topical or systemic infections which are caused by pathogenic fungi. The invention therefore is also directed to topical and systemic pharmaceutically acceptable compositions comprising an effective amount of a compound of formula I and a pharmaceutically acceptable carrier. In anothe aspect, this invention is directed to a method of controlling or preventing infections caused by pathogenic fungi by administering to a patient in need of such treatment a composition comprising an effective amount of a compound of formula I and a pharmaceuticlly acceptable carrier. Another aspect of this invention is directed to pharmaceutical compositions comprising, as the active ingredients, a compound of formula I and sterol biosynthesis inhibitors which are antimycotically active azoles or allylamines and a pharmaceutically acceptable carrier. Such combinations permit the use of significantly smaller amounts of each active ingredient than when they are used alone, to achieve the same or better results. Thus, the invention in another aspect is directed to controlling or preventing infections caused by pathogenic fungi by administering a composition comprising an effective amount of a combination of a compound of formula I and sterol bisynthesis inhibitors selected from antimycotically active azoles and allylamines. Preferred azoles are of the miconazole type, e.g., miconazole, ketoconazole, itraconazole and fluconazole.

Preferred allylamines are of the naftifine type, e.g., naftifine and terbinafine.

Yet another aspect of this invention is intermediates used for the preparation of these compounds of formula I.

DETAILED DESCRIPTION

The following terms used herein have the meaning which follow unless indicated otherwise in the text.

"Alkyl" is a straight or branched-chain saturated hydrocarbon residue with up to 10 carbon atoms, e.g. methyl, ethyl, propyl, isopropyl, t-butyl, pentyl and octyl. The variables in formula I have alkyls as follows:
$R^1$ and $R^2$—1-7 carbons, preferably 1-4 carbons;
$R^3$ and $R^4$—1-7 carbons, preferably $R^3$ is 1-4 carbons and $R^4$ is hydrogen;
$R^5$ and $R^6$—1-7 carbons, preferably 1-4 carbons;
Q—1-10 carbons, preferably 5-10 carbons, or when Q is phenyl or naphthyl, any alkyl substituent(s) thereon are 1-7 carbons, preferably 1-4 carbons;

"alkenyl" is a straight- or branched-chain hydrocarbon residue of 2-10 carbons, having an olefinic double bond, e.g. allyl, 2-butenyl, 4-methyl-3-pentenyl. The variables in formula I have alkenyls as follows:
$R^1$ and $R^2$—2-7 carbons, preferably 3-4 carbons;
Q—2-10 carbons, preferably 5-10 carbons;

"alkoxy" is an alkyl group as defined herein attached via an oxygen atom, e.g. methoxy, ethoxy;

"alkylene" is a straight- or branched-chain saturated hydrocarbon residue having two free valences, e.g. dimethylene, trimethylene and tetramethylene;

"halogen" is fluorine, chlorine, bromine or iodine.

"Leaving group" preferably is halogen, especially chlorine, bromine and iodine; and the trifluoromethylsulphonyloxy, lower alkylsulphonyloxy and arylsulphonyloxy groups, e.g. methylsulphonyloxy, benzenesulphonyloxy, p-toluene-sulphonyloxy and p-chlorophenylsulphonyloxy.

$R^1$ and $R^2$ each preferably are $C_{1-4}$-alkyl or $C_{3-4}$-alkenyl. $R^3$ preferably is hydrogen or $C_{1-4}$-alkyl. $R^4$ preferably is hydrogen. $R^5$ and $R^6$ each preferably are hydrogen, halogen or $C_{1-4}$-alkyl, especially hydrogen. Q preferably is a phenyl group, which is unsubstituted or substituted by one or two of halogen, especially bromine, chlorine or fluorine, trifluoromethyl, nitro, cyano, or $C_{1-4}$-alkyl; $C_{5-10}$-alkyl; $C_{5-10}$-hydroxyalkyl; or $C_{5-10}$-alkenyl.

Especially preferred compounds of formula I in the scope of the present invention are:
4'-[1-(Dimethylamino)ethyl]-4-biphenylyl phenyl ketone,
4-bromophenyl 4'-[(dimethylamino)methyl]-4-biphenylyl ketone,
4'-[(dimethylamino)methyl-4-biphenylyl 4-iodophenyl ketone,
4'-[1-(allylmethylamino)ethyl]-4-biphenylyl phenyl ketone,
4'-[1-(allylmethylamino)methyl]-4-biphenylyl 4-bromophenyl ketone,
4'-[1-(allylmethylamino)methyl]-4-biphenylyl 4-iodophenyl ketone, 2,4-difluorophenyl 4'-[(allylmethylamino)methyl]-4-biphenylyl ketone, 4'-[(dimethylamino)methyl]-4-biphenylyl 4-methyl-3-pentenyl ketone, 4'-[(allylmethylamino)methyl]-4-biphenylyl 4-methyl-3-pentenyl ketone and 4'-[(allylmethylamino)methyl]-4-biphenylyl 8-hydroxyoctyl ketone.

The compounds of formula I and their pharmaceutically acceptable acid addition salts can be prepared by utilizing the novel intermediates of formulas II, III, IV and XXIV in the following process:

a) reacting a compound of the formula

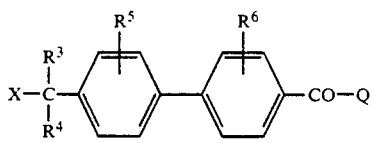

II wherein X is a leaving group as defined herein and $R^3$, $R^4$, $R^5$, $R^6$ and Q are as defined for formula I, with an amine of the formula $HNR^1R^2$, wherein $R^1$ and $R^2$ are as defined for formula I, or b) oxidizing a compound of the formula

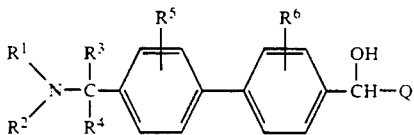

III wherein $R^1$, $R^2$, $R^3$, $R^4$, $R^5$, $R^6$ and Q are as defined for formula I, or c) treating a compound of the formula

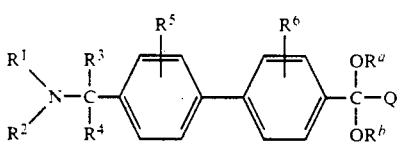

IV wherein $R^a$ and $R^b$ each are $C_{1-4}$-alkyl or together are dimethylene or trimethylene and $R^1$, $R^2$, $R^3$, $R^4$, $R^5$, $R^6$ and Q are as defined for formula I, with an aqueous acid, or d) reacting a compound of the formula

  X'—CO—Q    V wherein X' is halogen and Q is as defined for formula I, in the presence of a Lewis acid with a compound of the formula

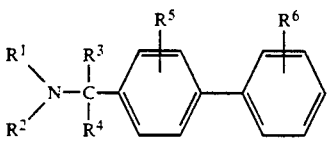

VI wherein $R^1$, $R^2$, $R^3$, $R^4$, $R^5$ and $R^6$ are as defined for formula I, or e) alkylating or alkenylating a compound of the formula

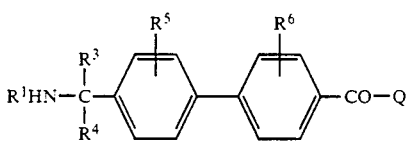

Ia wherein $R^1$, $R^3$, $R^4$, $R^5$, $R^6$ and Q are defined for formula I, or f) reacting a compound of the formula

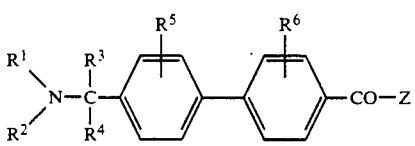

(XXIV)

wherein $R^1$, $R^2$, $R^3$, $R^4$, $R^5$ and $R^6$ are as defined for formula I and Z is a leaving group of the formula $NR^cR^d$ in which $R^c$ is lower alkyl and $R^d$ is lower alkyl or lower alkoxy, (wherein "lower" means from 1 to 7 carbons)

with a compound of the formula M—Q in which M is —MgCl, —MgBr, —MgI or —Li and Q is as defined for formula I, and g) if desired, converting a compound of formula I obtained into a pharmaceutically acceptable acid addition salt.

The reaction of a compound of formula II with an amine of the formula $HNR^1R^2$ in accordance with process variant a) can be carried out by conventional means. The reaction is preferably carried out in a polar solvent and in the presence of a base as the acid-binding agent in a temperature range of about 0° C. to about 150° C. Suitable polar solvents are, for example, lower alcohols such as methanol and ethanol and lower dialkyl ketones such as acetone. Suitable bases are, for example, molar excess of amines of the formula $HNR^1R^2$, tertiary amines such as triethylamine and inorganic bases such as alkali metal carbonates, alkali metal hydroxides and alkali metal alcoholates, e.g. sodium or potassium carbonate or hydroxide and sodium or potassium methylate or ethylate.

The oxidation of a compound of formula III in accordance with process variant b) can be carried out by conventional means. The reaction is preferably carried out in an inert solvent and in the presence of an oxidation agent in a temperature range of about −80° C. to about room temperature. Suitable inert solvents are, for example, chlorinated lower hydrocarbons such as methylene chloride and chloroform. Suitable oxidation agents are, for example, manganese dioxide or mixtures of dimethyl sulphoxide with oxalyl chloride, dicyclohexyl-carbodiimide or acetic anhydride and a tertiary amine such as triethylamine.

A dilute, aqueous mineral acid, e.g. dilute hydrochloric acid, is preferably used for the treatment of a compound of formula IV with an aqueous acid in accordance with process variant d) and the treatment is preferably carried out in a temperature range of about 0° C. to about room temperature.

The reaction of a compound of formula V with a compound of formula VI in accordance with process variant d) can be carried out by conventional means. The reaction is preferably carried out in an inert solvent and in the presence of a Lewis acid in a temperature range of about 0° C. to about 100° C. Suitable inert solvents are, for example, halogenated lower hydrocarbons such as methylene chloride, chloroform and ethylene chloride, nitrobenzene and carbon disulphide. Aluminium chloride is preferably used as the Lewis acid. Especially suitable compounds of formula V are the corresponding carboxylic acid chlorides.

The alkylation or alkenylation of a compound of formula Ia in accordance with process variant e) can be carried out by conventional means. The reaction is preferably carried out in the presence of a base, in a polar solvent and in a temperature range of about 0° C. to about 100° C. Suitable polar solvents are, for example, lower alcohols such as methanol and ethanol; lower dialkyl ketones such as acetone; dimethylformamide; and mixtures thereof with water. Alkali metal carbonates and alkali metal hydroxides such as potassium carbonate and sodium hydroxide are preferably used as the bases.

The reaction of a compound of formula XXIV in accordance with process variant f) can be carried out by conventional means. The reaction is preferably carried out in an inert solvent and in a temperature range of about −80° C. to about room temperature. Suitable inert solvents are, for example, open-chain and cyclic ethers such as diethyl ether, methyl t-butyl ether and tetrahydrofuran and mixtures thereof.

The manufacture of pharmaceutically acceptable acid addition salts of compounds of formula I in accordance with process variant g) can be carried out by conventional means. Thus, the compounds of formula I form acid addition salts with pharmaceutically acceptable inorganic and organic acids such as the following which form the preferred salts, hydrochloric acid, hydrobromic acid, sulfuric acid, nitric acid, citric acid, acetic acid, succinic acid, fumaric acid, methansulphonic acid and p-toluenesulphonic acid.

The various compounds which are used as starting materials can be prepared, for example, in accordance with the following Reaction Schemes I-VI and the following descriptions of the various reactions. In these Reaction Schemes $R^1$, $R^2$, $R^3$, $R^4$, $R^5$, $R^6$, $R^a$, $R^b$, Q, X and X' have the meanings indicated above. M is —Li, —MgCl, —MgBr or —MgI, $R^{31}$ and $R^{41}$ each is lower alkyl, X'' is a trifluoromethylsulphonyloxy, a lower alkylsulphonyloxy or arylsulphonyloxy group and X''' is a halogen atom or a trifluoromethylsulphonyloxy group.

Reaction Scheme I

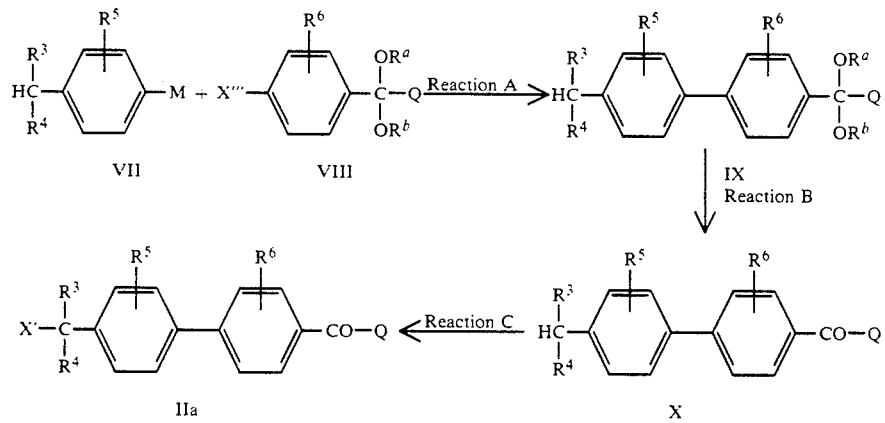

Reaction Scheme II

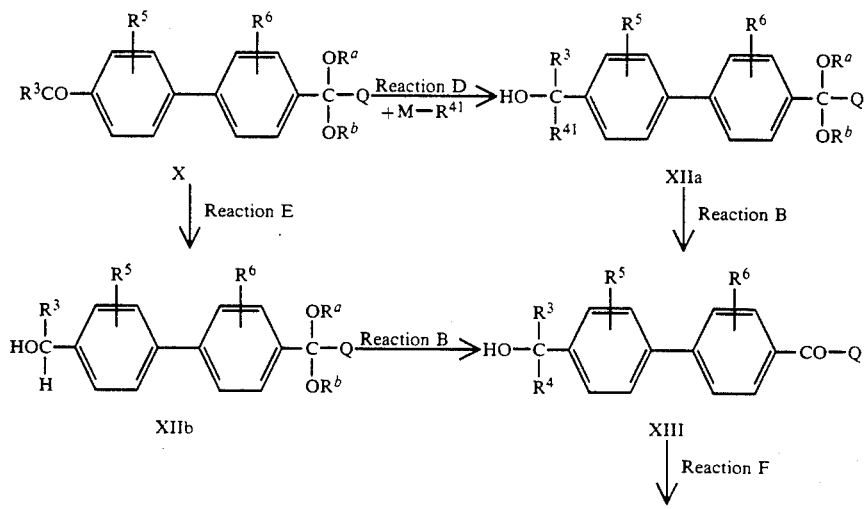

-continued
Reaction Scheme II
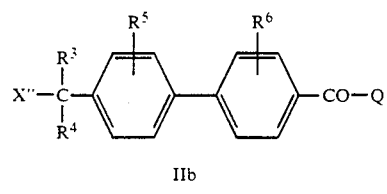
IIb
Reaction Scheme III
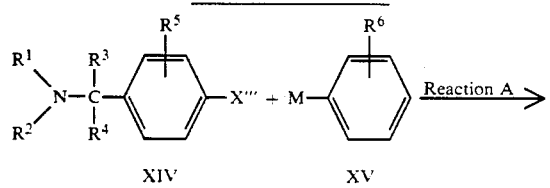
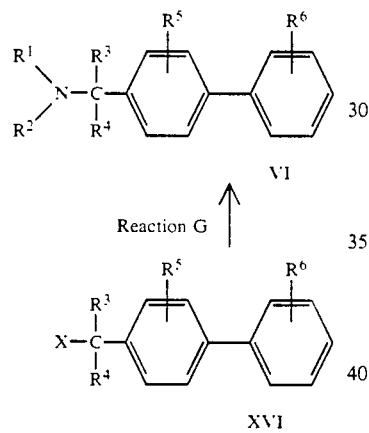
Reaction Scheme IV
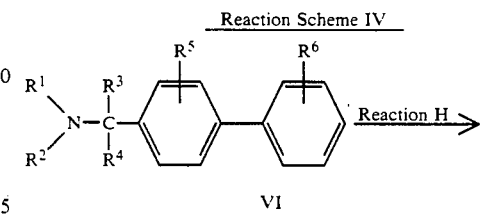
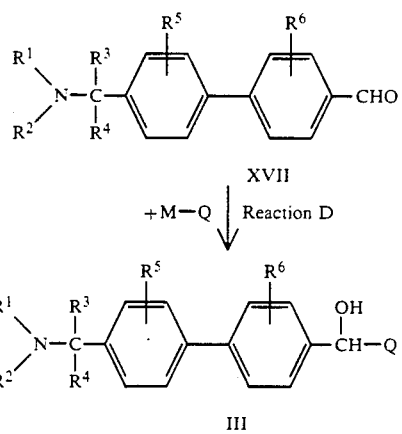
Reaction Scheme V
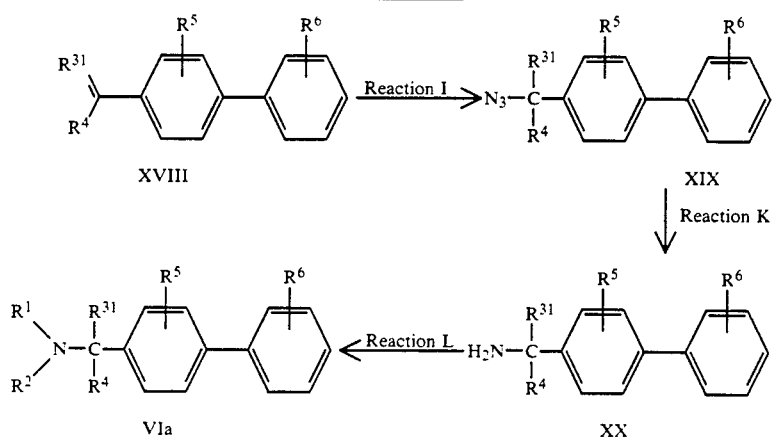

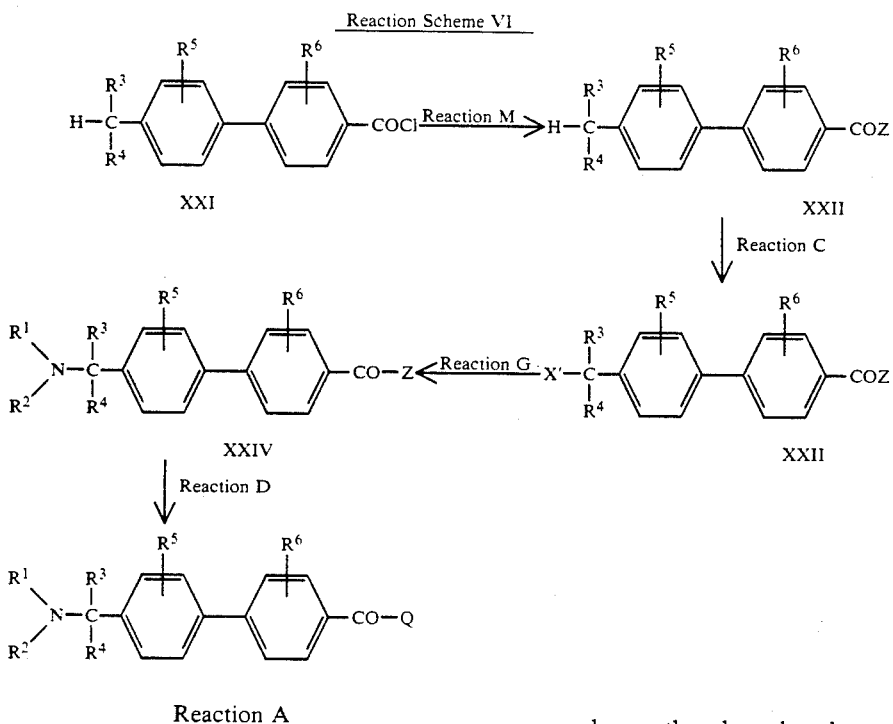

Reaction Scheme VI

Reaction A

This reaction can be carried out by conventional means. It is preferably carried out in an inert solvent at a temperature range of 20° C. to 100° C. and in the presence of a suitable catalyst. The symbol M preferably signifies —MgBr and X''' preferably signifies bromine. As catalysts there are preferably used Pd catalysts such as tetrakis(triphenyl-phosphine)palladium or Ni catalysts (see D. A. Widdowson and Y. Z. Zhang, Tetrahedron 42, 2111 (1986)). An open-chain or cyclic ether such as diethyl ether, dimethoxyethane and tetrahydrofuran is preferably used as the solvent.

Reaction B

This reaction is preferably carried out by treatment with an aqueous acid. A dilute, aqueous mineral acid, e.g. dilute hydrochloric acid, is preferably used and the reaction is carried out at a temperature range of about 0° C. to about room temperature.

Reaction C

This halogenation can be carried out by conventional means. The reaction is preferably carried out in a chlorinated, lower hydrocarbon such as carbon tetrachloride or chloroform at a temperature range of 0° C. to 100° C. using N-bromosuccinimide or elementary bromine or chlorine. The reaction can be catalyzed by light or radical-initiators such as azaisobutyronitrile.

Reaction D

This reaction can be carried out by conventional means. It is preferably carried out in an inert solvent at a temperature range of 0° C. to 80° C. An open-chain or cyclic ether such as diethyl ether, dimethoxyethane and tetrahydrofuran is preferably used as the solvent, M is preferably —MgBr and R''' is preferably ethyl.

Reaction E

This reaction can be carried out by conventional means. It is preferably carried out in a polar solvent such as methanol or ethanol at a temperature range of 0° to 50° C. As reduction agents there are preferably used complex borohydrides such as sodium borohydride, however, elementary hydrogen in the presence of transition metal catalysts can also be used.

Reaction F

This reaction can be carried out by conventional means. In a preferred embodiment pyridine or picoline is used as the solvent and the reaction is carried out at a temperature range of 0° C. to 50° C. Trifluoromethylsulphonic anhydride, a lower alkylsulphonyl chloride or an arylsulphonyl chloride is preferably used as the reagent.

Reaction G

This reaction is carried out using an amine of the formula $HNR^1R^2$. It can be carried out by conventional means. The reaction is preferably carried out in a polar solvent and in the presence of a base as an acid-binding agent in a temperature range of about 0° C. to about 150° C. Suitable polar solvents are, for example, lower alcohols such as methanol and ethanol and lower dialkyl ketones such as acetone. Suitable bases are, for example, excess amine of the formula $HNR^1R^2$, tertiary amines such as triethylamine and inorganic bases such as alkali metal carbonates, alkali metal hydroxides and alkali metal alcoholates.

Reaction H

This formylation can be carried by conventional means. It is preferably carried out in a strong organic acid, such as e.g. trifluoroacetic acid, as the solvent at a temperature range of 0° C. to 90° C. As the reagent there is used e.g. hexamethylenetetramine, see W. E. Smith, J. Org. Chem. 37, 3972 (1972). The formylation can, however, also be carried out according to Vilsmeyer using disubstituted formamides such as e.g. N,N-dimethylformamide and phosphorous oxychloride, see C. Jutz, Adv. Org. Chem. 9, 225 (1976). Finally, it can also be carried out using a formylating reagent, such as e.g. dichloromethyl methyl ether or triethyl orthoformate, in the presence of a Lewis acid, such as aluminium chloride, in an inert solvent, such as dichloromethane, at a temperature range of 0° C. to 40° C.

Reaction I

This reaction is carried out using an alkali metal azide, preferably sodium azide, in a conventional manner. A chlorinated lower hydrocarbon, such as chloroform and 1,2-dichloroethane, is preferably used as the solvent. The reaction is preferably carried out in the presence of a strong acid, such as trifluoroacetic acid and sulphuric acid, at a temperature range of −10° C. to 20° C. (see D. Baldermann and A. Kadic, Synthesis 1978, 24).

Reaction K

This reaction is a conventional reduction. In a preferred embodiment, Raney-nickel in a lower alcohol, such as isopropanol, is used and the reduction is carried out at a temperature range of 0° C. to 100° C. (see D. Baldermann and A. Kadic, Synthesis 1978, 24).

Reaction L

This reaction is a conventional alkylation or alkenylation. It can be carried out by conventional means. The reaction is preferably carried out in the presence of a base, in a polar solvent in a temperature range of about 0° C. to about 100° C. Suitable solvents are, for example, lower alcohols such as methanol and ethanol, lower dialkyl ketones such as acetone, dimethylformamide and mixtures thereof with water. Alkali metal carbonates and alkali metal hydroxides such as potassium carbonate and sodium hydroxide are preferably used as the bases.

Reaction M

This reaction is a conventional carboxamidation which can be carried out by reaction with an amine of the formula $HNR^cR^d$ or a salt of this amine. A chlorinated, lower hydrocarbon such as chloroform of methylene chloride is preferably used as the solvent. The reaction is preferably carried out in the presence of an organic base such as pyridine or triethylamine in a temperature range of −10° C. to 20° C. (see S. Nahm and S. M. Weinreb, Tetrahedron Lett. 1981, 22 3815). Lower alkyl or alkoxy groups $R^c$ or $R^d$ are preferably methyl or methoxy.

The compounds of formula I and their pharmaceutically acceptable acid addition salts have valuable antifungal properties. They are active against a large number of pathogenic fungi which cause topical and systemic infections, such as Candida albicans and Histoplasma capsulatum. 2,3-Epoxysqualene-lanosterol cyclase, an enzyme involved in the sterol biosynthesis of eucaryotic cells, is an essential enzyme for the fungi. Thus e.g. a S. cerevisiae strain in which this enzyme is absent is not viable [F. Karst & F. Lacroute, Molec. Gen. Genet. 154, 269 (1977)]. The inhibitory action of the compounds of formula I on the above-mentioned enzyme from C. albicans was taken as the measurement for the antifungal activity. The inhibition can be measured, for example, by means of the method described hereinafter.

Determination of the IC50 value for the inhibition of 2,3-epoxysqualene-lanosterol cyclase from Candida albicans The cells of a culture of Candida albicans were collected at the end of the logarithmic growth phase and washed with 100 mM phosphate buffer (pH=6.9), digestion buffer and 50 mM phosphate buffer (pH=7.4) containing 1M mannitol and 5 mM DTT (dithiothreitol).

1.0 g of these cells was suspended in 5 ml of digestion buffer, treated with 1 mg of Zymolase 100T (Seikagaku Kogyo, Japan) and 12.5 μl of β-mercaptoethanol and incubated at 30° C. for 30 minutes. The resulting protoplasts were isolated by centrifugation (10 minutes at 2500 g) and subsequently ruptured by the addition of 2 mL of 100 mM phosphate buffer (pH=6.9). By renewed centrifugation (10 minutes at 10000 g) there was obtained a cell-free extract (CFE) as the supernatant. This was diluted to 10 mg of protein per ml and the pH is brought to 6.9.

The activity of the 2,3-eoxysqualene-lanosterol cyclase in the CFE was measured by reacting $^{14}C$-squalene epoxide in the presence of n-decylpentaoxyethylene as a detergent. Titration with measured amounts of the test substance permits the determination of the $IC_{50}$ value (concentration of test substance which reduces the enzyme activity by half).

The test was carried out as follows:

A 250 μM solution of $^{14}C$-squalene epoxide in 100 mM phosphate buffer (pH=6.9) with the addition of 1% n-decylpentaoxyethylene was prepared by ultrasonic treatment. 100 μL of this solution were treated with 20 μL of a solution of the test substance in dimethyl sulphoxide (or 20 μL of pure dimethyl sulphoxide as the control). After the addition of 880 μL of CFE the well-mixed solution was incubated at 30° C. for 1 hour while shaking. Subsequently, the reaction was stopped by the addition of 500 μL of 15 percent potassium hydroxide in 90 percent ethanol.

The mixture was extracted twice with 1 mL of n-hexane, the hexane was evaporated and the lipid residue was taken up in 200 μL of diethyl ether. After thin-layer chromatography on silica gel using methylene chloride as the eluant the plates were investigated using a radioactive thin-layer scanner.

Only lanosterol was found as the radioactive product under the conditions used. Its amount was compared with the amount of radioactive lanosterol in the control.

The $IC_{50}$ values were determined graphically and were given in μg of test substance per mL. Table I hereinafter contains $IC_{50}$ values determined in the above test for representative members of the class of compound defined by formula I as well as concerning the acute toxicity in the case of single oral administration to mice ($LD_{50}$ in mg/kg).

TABLE I $$R^1R^2N-CR^3R^4-C_6H_3(R^5)-C_6H_3(R^6)-CO-Q$$

| No | $R^1$ | $R^2$ | $R^3$ | $R^4$ | $R^5$ | $R^6$ | Q | $IC_{50}$ in μg/mL | $LD_{50}$ in mg/kg |
|---|---|---|---|---|---|---|---|---|---|
| 1 | —CH₃ | —CH₃ | H | H | H | H | Ph | 0.100 | |
| 2 | " | " | —CH₃ | " | " | " | " | 0.080 | |
| 3 | " | " | H | " | " | " | 4-Fluoro-Ph | 0.100 | |
| 4 | " | " | " | " | " | " | 2,4-Dichloro-Ph | 0.077 | |
| 5 | " | " | " | " | " | " | 4-Nitro-Ph | 0.115 | |
| 6 | " | " | " | " | " | " | 4-Bromo-Ph | 0.044 | |
| 7 | " | " | " | " | " | 2-Cl | 2,4-Dichloro-Ph | 0.100 | |
| 8 | " | " | " | " | " | H | 2-Chloro-4-nitro-Ph | 0.044 | |
| 9 | " | " | —CH₃ | —CH₃ | " | " | Ph | 0.950 | |
| 10 | " | " | H | H | " | " | 4-Iodo-Ph | 0.047 | |
| 11 | " | " | " | " | " | " | 4-Cyano-Ph | 0.058 | |
| 12 | " | " | " | " | " | " | 1-Na | 0.310 | |
| 13 | " | " | " | " | " | " | 2-Na | 0.210 | |
| 14 | Allyl | " | " | " | " | " | Ph | 0.018 | >4000 |
| 15 | " | " | " | " | " | " | 4-Fluoro-Ph | 0.036 | |
| 16 | " | " | " | " | " | " | 2,4-Dichloro-Ph | 0.016 | |
| 17 | " | " | " | " | " | " | 4-Nitro-Ph | 0.016 | |
| 18 | " | " | —CH₃ | " | " | " | Ph | 0.032 | |
| 19 | " | " | H | " | " | " | 4-Cyano-Ph | 0.040 | |
| 20 | " | " | " | " | " | " | 4-Bromo-Ph | 0.013 | |
| 21 | " | " | " | " | " | 2-Cl | 2,4-Dichloro-Ph | 0.026 | |
| 22 | " | " | " | " | " | H | 1-Na | 0.170 | |
| 23 | " | " | " | " | " | " | 2-Na | 0.160 | |
| 24 | " | —CH₃ | " | " | " | " | 2-Chloro-4-nitro-Ph | 0.011 | |
| 25 | —CH₂CH₃ | " | " | " | " | " | Ph | 0.045 | |
| 26 | H | " | " | " | " | " | " | 0.200 | |
| 27 | —CH₃ | " | " | " | " | " | 2,4-Dibromo-Ph | 0.024 | |
| 28 | Allyl | " | " | " | " | " | 2,4-Dibromo-Ph | 0.02 | |
| 29 | —CH₃ | " | " | " | " | " | 2-Methoxy-Ph | 0.19 | |
| 30 | " | " | " | " | " | " | 2,4-Difluoro-Ph | 0.029 | |
| 31 | Allyl | " | " | " | " | " | 2,4-Difluoro-Ph | 0.008 | |
| 32 | —CH₃ | " | " | " | " | " | 2-Methyl-Ph | 0/03 | |
| 33 | Allyl | " | " | " | " | " | 2-Methyl-Ph | 0.012 | |
| 34 | " | " | " | " | " | " | 2-Methyl-Ph | 0.018 | |
| 35 | —CH₃ | " | " | " | " | " | n-Pentyl | 0.031 | |
| 36 | " | " | " | " | " | " | 4-Methyl-3-pentenyl | 0.003 | |
| 37 | " | " | " | " | " | " | 8-Hydroxyoctyl | 0.017 | |
| 38 | Allyl | " | " | " | " | " | n-Pentyl | 0.021 | |
| 39 | Allyl | " | " | " | " | " | 4-Methyl-3-pentenyl | 0.009 | |
| 40 | " | " | " | " | " | " | 8-Hydroxyoctyl | 0.007 | |

Ph = Phenyl
Na = Naphthyl

The synergistic activity of the compounds of formula I and their pharmaceutically acceptable acid addition salts in combination with sterol biosynthesis inhibitors such as ketoconazole can be demonstrated, for example, by means of the agar dilution method. For this purpose there were used casitone agar and inocula (10 cells/ml) of culture of Candida albicans which were 48 hours old. The test substances (TS, compounds of formula I) were applied in concentrations of 80–1.25 μg/mL and the sterol biosynthesis inhibitors (SBI) were applied in concentrations of 20–0.001 μg/mL, with the dilution series being in each case 1:2. The cultures were incubated at 37° C. for 2 days. The minimum inhibitory concentrations (MIC) of the various active substances were then determined in the case of the application alone as well as in the case of the combined application and the fractional inhibitory concentration (FIC) was calculated according to the following formula from the MIC values determined:

$$FIC = \frac{MIC\ (TS\ alone)}{MIC\ (TS\ in\ combination)} + \frac{MIC\ (SBI\ alone)}{MIC\ (SBI\ in\ combination)}$$

A synergistic effect is present when the FIC is <0.5. The data contained in Table II hereinafter for compounds 14 and 20 according to Table I, representative members of the class of compounds defined by formula I, in combination with ketoconazole or terbinafine, representative sterol biosynthesis inhibitors, confirm the synergistic activity.

TABLE II

| C. albicans | MIC in μg/mL Compound alone | | Compound in combination | | FIC |
|---|---|---|---|---|---|
| | 20/ketoconazole | | 20/ketoconazole | | |
| $H_{12}$ | 2 | 5 | 0.25 | 0.15 | 0.156 |
| | | | 0.12 | 0.075 | 0.078 |
| $H_{29}$ | 1 | 0.15 | 0.25 | 0.019 | 0.375 |
| 3153 | 1 | 2.5 | 0.12 | 0.075 | 0.156 |
| $B_5$ | 1 | 0.15 | 0.25 | 0.019 | 0.25 |
| $B_4$ | 2 | 2.5 | 0.12 | 0.075 | 0.093 |
| | 20/terbinafine | | 20/terbinafine | | |
| $H_{12}$ | 2 | 6 | 0.25 | 0.75 | 0.25 |
| $H_{29}$ | 1 | 3.1 | 0.25 | 0.75 | 0.50 |
| 3153 | 1 | 6 | 0.12 | 1.50 | 0.375 |
| $B_5$ | 1 | 3.1 | 0.25 | 0.7 | 0.5 |

TABLE II-continued

| C. albicans | MIC in μg/mL | | | | |
|---|---|---|---|---|---|
| | Compound alone | | Compound in combination | | FIC |
| B4 | 2 | 100 | 0.50 | 1.5 | 0.266 |
| | | 14/ ketoconazole | | 14/ ketoconazole | |
| H12 | 1 | 10 | 0.12 | 0.075 | 0.133 |
| | | | 0.06 | 0.6 | 0.125 |
| H29 | 1 | 0.15 | 0.06 | 0.019 | 0.187 |
| | | | 0.12 | 0.038 | 0.375 |
| 3153 | 1 | 2.5 | 0.06 | 0.6 | 0.187 |
| | | | 0.12 | 0.075 | 0.156 |
| B5 | 1 | 0.3 | 0.06 | 0.019 | 0.125 |
| | | | 0.12 | 0.038 | 0.25 |
| B4 | 2 | 5 | 0.12 | 0.075 | 0.078 |
| | | | 0.06 | 0.15 | 0.40 |
| | | 14/terbinafine | | 14/terbinafine | |
| H12 | 1 | 100 | 0.5 | 1.5 | 0.516 |
| H29 | 1 | 25 | 0.25 | 3.0 | 0.375 |
| 3153 | 1 | 100 | 0.25 | 3.0 | 0.281 |
| | | | 0.25 | 1.5 | 0.561 |
| B5 | 1 | 25 | 0.25 | 3.0 | 0.375 |
| B4 | 2 | 100 | 1 | 3.0 | 0.531 |

The compounds of formula I and their pharmaceutically acceptable acid addition salts can be used as medicaments, e.g. in the form of pharmaceutical compositions and dosage forms for enteral, parenteral or topical administration. They can be administered, for example, perorally, e.g. in the form of tablets, coated tablets, dragees, hard and soft gelatin capsules, solutions, emulsions or suspensions, rectally, e.g. in the form of suppositories, parenterally, e.g. in the form of injection solutions or infusion solutions, or topically, e.g. in the form of salves, creams or oils.

The manufacture of the pharmaceutical preparations can be effected in a conventional manner by incorporating the compounds of formula I and their pharmaceutically acceptable acid addition salts, optionally in combination with other therapeutically valuable substances, for example, the aforementioned sterol biosynthesis inhibitors, into a galenical dosage form together with suitable, nontoxic, inert, therapeutically compatible solid or liquid carrier materials and, if desired, the usual pharmaceutical adjuvants.

Suitable sterol biosynthesis inhibitors for combination with compounds of formula I are, for example, the systemic, antifungally-active azoles of the miconazole type, e.g. keto- conazole, itraconazole and fluconazole, and the systemic, antifungally-active allylamines of the naftifine type, e.g. naftifine and terbinafine.

Suitable carrier materials are not only inorganic carrier materials, but also organic carrier materials. Thus, lactose, maize starch or derivatives thereof, talc, stearic acid or its salts can be used, for example, as carrier materials for tablets, coated tablets, dragees and hard gelatin capsules. Suitable carrier materials for soft gelatin capsules are, for example, vegetable oils, waxes, fats and semi-solid and liquid polyols (depending on the nature of the active substance no carriers are, however, required in the case of soft gelatin capsules). Suitable carrier materials for solutions and syrups are, for example, water, polyols, saccharose, invert sugar and glucose. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrog-enated oils, liquid waxes, liquid paraffins, liquid fatty alcohols, sterols, polyethylene glycols and cellulose derivatives.

The usual stabilizing, preserving, wetting and emulsifying agents, consistency-improving agents, flavor-improving agents, salts for varying the osmotic pressure, buffer substances, solubilizers, coloring and coating agents and antioxidants can be used as pharmaceutical adjuvants.

The dosage of the compounds of formula I can vary within wide limits depending on the pathogenic fungi to be controlled, the age and the individual condition of the patient and the mode of administration and will, of course, be fitted to the individual requirements in each particular case by the attending clinician. In the case of adult patients a daily dosage of about 0.01 g to about 4 g, especially about 0.05 g to about 2 g, is suitable for the prevention and control of topical and systemic infections by pathogenic fungi. Depending on the dosage it is convenient to administer the daily dosage in several dosage units. In the case of combination therapy a daily dosage of about 0.01 g to about 2 g, especially about 0.02 to about 1 g, of a compound of formula I and of about 0.02 g to about 0.2 g of a sterol biosynthesis inhibitor is suitable.

The pharmaceutical preparations with the compounds of formula I as the sole active ingredient conveniently contain about 10-1000 mg, preferably 50-500 mg, of a compound of formula I. The combination preparations conveniently contain about 10-500 mg, preferably 20-250 mg, of a compound of formula I and about 50-100 mg of a sterol biosynthesis inhibitor.

The following Examples illustrate the present invention in more detail. They are, however, not intended to limit its scope in any manner. Unless indicated otherwise, all examples were carried out as written. All temperatures are given in degrees Celsius.

EXAMPLE 1 a) A mixture of 100 g of 4-bromobenzophenone, 25 g of ethylene glycol and 3.35 g of p-toluenesulphonic acid in 625 mL of benzene was heated to boiling under reflux for 6 days, with the water formed being removed continuously. The mixture obtained was evaporated and the solid was recrystallized from hexane. There was obtained 85.9 g (74%) of the ethylene glycol ketal of 4-bromo-benzophenone with a m.p. of 58°-62° C.

b) A mixture of 1.28 g of palladium(II) acetate and 6.64 g of triphenylphosphine in 120 mL of tetrahydrofuran was heated to boiling under reflux for 0.5 hour. The mixture was treated with 35 g of the ethylene glycol ketal of 4-bromobenzophenone. Subsequently, the Grignard reagent obtained from 4.19 g of magnesium and 29.4 g of 4-bromotoluene in 180 mL of tetrahydrofuran was added slowly to the boiling solution. After completion of the addition the mixture was heated to boiling under reflux for a further 3 hours. The mixture was evaporated and the residue was taken up in 320 mL of ethanol and 290 ml of 2N aqueous hydrochloric acid. The mixture was heated to boiling for 4 hours and then evaporated. The residue was recrystallized from ethanol, there was obtained 26 g (83%) of 4-benzoyl-4'-methylbiphenyl with a m.p. of 124°-125° C.

c) A mixture of 26.1 g of 4-benzoyl-4'-methylbiphenyl, 18.6 g of N-bromosuccinimide and 0.18 g of azaisobutyronitrile in 600 mL of carbon tetrachloride was heated to boiling for 4 hours. The brown solution obtained was filtered and evaporated. The residue was recrystallized from cyclohexane. There are obtained 29.9 g (89%) of 4'-(bromomethyl)-4-biphenylyl phenyl ketone as colorless crystals with a m.p. of 110°–112° C.

d) 516 mg of 4'-(bromomethyl)-4-biphenylyl phenyl ketone were dissolved in a 33 percent solution of dimethylamine in ethanol. The solution was stirred at room temperature overnight and then evaporated. The residue was treated with aqueous sodium carbonate solution and the product was extracted with ether. The extracts were dried over magnesium carbonate and treated with a 22 percent solution of hydrogen chloride in ether. The precipitated hydrochloride was filtered off and dried. There was obtained 280 mg (54%) of 4'-[(dimethylamino)methyl]-4-biphenylyl phenyl ketone hydrochloride as a yellowish solid with a m.p. of 226°–230° C.

EXAMPLE 2 a) 3.0 g 4'-(bromomethyl)-4-biphenylyl phenyl ketone were dissolved in 100 mL of ethanol and treated with 0.72 g of N-allylmethylamine and 1.17 g of potassium carbonate. The mixture was heated to boiling under reflux for 5 hours, evaporated and extracted with ether. The extracts were dried and treated with a 22 percent solution of hydrogen chloride in ether. The precipitated product was filtered off and dried. There was obtained 3.22 g (68%) of 4'-[(allylmethylamino)methyl-4-biphenylyl phenyl ketone hydrochloride as a colorless solid with a m.p. of 138°–140° C.

The compounds described hereinafter were manufactured in an analogous manner:

b) 4'-[(Diallylamino)methyl]-4-biphenylyl phenyl ketone as a yellowish oil after purification by chromatography on silica gel using hexane/ethyl acetate 7:3 as the elution agent. Yield 53%. Mass spectrum: peaks at, inter alia, m/e 367 (M+, 19%), 271 (100%), 165 (22%).

c) 4'-[Ethylmethylamino)methyl]-4-biphenylyl phenyl ketone hydrochloride as a colorless solid with a m.p. of 258° C. Yield 66%.

d) 4'-[(Methylamino)methyl]-4-biphenylyl phenyl ketone hydrochloride as a colorless solid with a m.p. of 267° C. Yield 55%.

e) 4'-[[[2-Butenyl]methylamino]methyl]-4-biphenylyl phenyl ketone hydrochloride as a colorless solid with a m.p. of 120° C. Yield 22%.

f) 4'-[[(2-Methylallyl)methylamino]methyl]-4-biphenylyl phenyl ketone hydrochloride as a colorless solid with a m.p. of 146° C. Yield 89%.

g) 4'-[(Propylamino)methyl]-4-biphenylyl phenyl ketone hydrochloride as a colorless solid with a m.p. of 260° C. Yield 58%.

h) 4'-[(Methylpropylamino)methyl]-4-biphenylyl phenyl ketone hydrochloride as a colorless solid with a m.p. of 154° C. Yield 26%.

EXAMPLE 3 a) 1.06 g of palladium(II) acetate and 5.48 g of triphenylphosphine were dissolved in 100 mL of tetrahydrofuran. The solution was treated with 29 g of the ethylene glycol ketal of 4-bromobenzophenone and the mixture was heated to boiling under reflux. Subsequently, a solution of the Grignard reagent obtained from 26.3-g of 4-ethylbromobenzene and 3.46 g of magnesium in 100 mL of tetrahydrofuran was added slowly to the above boiling solution. The mixture was heated to boiling under reflux for a further 3 hours and then worked up as described in Example 1b). After chromatography on silica gel with toluene/hexane 7:3 as the elution agent there were obtained 19.15 g (70%) of 4'-ethyl-4-benzoyl-biphenyl as a colorless solid with a m.p. of 106°–108° C.

b) 19 g of 4'-ethyl-4-benzoyl-biphenyl, 12.4 g of N-bromosuccinimide and 0.12 g of azaisobutyronitrile in 400 mL of carbon tetrachloride were heated to boiling under reflux for 1.5 hours. After filtering off the precipitated material the solution was evaporated and the residue was recrystallized from cyclohexane. There were obtained 20.7 g (85%) of 4'-(1-bromo-ethyl)-4-benzoyl-biphenyl as a colorless solid with a m.p. of 132°–134° C.

c) In analogy to Example 1d) there was obtained therefrom rac-4'-[1-(dimethylamino)ethyl]-4-biphenylyl phenyl ketone hydrochloride as a yellowish solid with a m.p. of 239°–241° C. Yield 57%.

The compounds listed hereinafter were manufactured in an analogous manner:

d) rac-4'-[1-(Allylmethylamino)ethyl]-4-biphenylyl phenyl ketone hydrochloride as a colorless solid with a m.p. of 88°–92° C. Yield 35%.

e) 4'-[(Dimethylamino)methyl]-3'-methyl-4-biphenylyl phenyl ketone hydrochloride as a colorless solid with a m.p. of 221°–222° C. Yield 15%.

f) rac-4'-[1-(Pyrrolidino)ethyl]-4-biphenylyl phenyl ketone hydrochloride as a colorless solid with a m.p. of 184° C. Yield 14%.

g) 4'-[[(2-Methylallyl)methylamino]methyl]-3'-methyl-4-biphenylyl phenyl ketone hydrochloride as a colorless solid with a m.p. of 107°–109° C. Yield 13%.

EXAMPLE 4 a) 35 mL of nitrobenzene were cooled in an ice bath and then treated in succession with 5.2 g of aluminium chloride and 5.0 g of 4-methylbiphenyl. The mixture was brought to room temperature and then treated slowly with 7.7 g of 2,4-dichlorobenzoyl chloride. The mixture was stirred at room temperature overnight, poured into water and extracted with methylene chloride. The extracts were washed with 2N hydrochloric acid and water, dried over magnesium sulphate and evaporated. The residue was chromatographed on silica gel with toluene/ethyl acetate 9:1. There were obtained 6.7 g (63%) of 2,4-dichlorophenyl 4'-methyl-4-biphenylyl ketone as a colorless solid with a m.p. of 184°–185° C.

b) A mixture of 5.0 g of 2,4-dichlorophenyl 4'-methyl-4-biphenylyl ketone, 2.7 g of N-bromosuccinimide and 20 mg of azaisobutyronitrile in 70 mL of carbon tetrachloride was heated to boiling under reflux for 4 hours. The precipitated material was filtered off and the filtrate was evaporated. The residue was recrystallized from toluene/cyclohexane. There were obtained 5.5 g (89%) of 2,4-dichlorophenyl 4'-bromomethyl-4-biphenylyl ketone as a colorless solid with a m.p. of 92° C.

c) 1.0 g of 2,4-dichlorophenyl 4'-bromomethyl-4-biphenylyl ketone and 20 mL of a 33 percent solution of dimethylamine in ethanol were heated to boiling for 4 hours, whereupon the mixture was evaporated. The residue was taken up in ether and treated with an ethereal solution of hydrogen chloride. The precipitated hydrochloride was filtered off and dried. There was obtained 2,4-dichlorophenyl 4'-[(dimethylamino)methyl]-4-biphenylyl ketone hydrochloride with a m.p. of 195°–196° C. Yield 51%.

The compounds listed hereinafter were manufactured in an analogous manner:

d) 4'-[(Dimethylamino)methyl]-4-biphenylyl p-fluorophenyl ketone hydrochloride with a m.p. of 230° C. Yield 41%.

e) 4'-[(Dimethylamino)methyl]-4-biphenylyl 1-naphthyl ketone hydrochloride with a m.p. of 226° C. Yield 50%.

f) 4'-[(Dimethylamino)methyl]-4-biphenylyl 2-naphthyl ketone hydrochloride with a m.p. of 263° c. Yield 54%.

g) 4'-[(Dimethylamino)methyl]-4-biphenylyl p-nitrophenyl ketone hydrochloride with a m.p. of 228° C. Yield 64%.

h) p-[[(4'-[(Dimethylamino)methyl]-4-biphenylyl]carbonyl]benzonitrile hydrochloride with a m.p. of 243° C. Yield 59%.

i) p-Bromophenyl 4'-[(dimethylamino)methyl]-4-biphenylyl ketone hydrochloride with a m.p. of 253° C. Yield 48%.

j) 4'-[(Dimethylamino)methyl]-4-biphenylyl p-iodophenyl ketone hydrochloride with a m.p. >250° C. Yield 48%.

k) 2-Chloro-4-nitrophenyl 4'-[(dimethylamino)methyl]-4-biphenylyl ketone hydrochloride with a m.p. of 223° C. Yield 63%.

l) 2-Bromo-4-chlorophenyl 4'-[(dimethylamino)methyl]-4-biphenylyl ketone hydrochloride with a m.p. of 227° C. Yield 61%.

EXAMPLE 5 a) 1.0 g of 2,4-dichlorophenyl 4'-bromomethyl-4-biphenylyl ketone, 1.5 mL of N-allylmethylamine and 0.84 g of potassium carbonate in 25 mL of ethanol were heated to boiling under reflux for 4 hours. The mixture was evaporated and the residue was extracted with ether. The extracts were dried over magnesium suphate and treated with an ethereal solution of hydrogen chloride. The precipitated hydrochloride was filtered off and dried. There was obtained 2,4-dichlorophenyl 4'-(allylmethylamino)-methyl]-4-biphenylyl ketone hydrochloride as a yellowish solid with a m.p. of 175°-176° C.

The compounds described hereinafter were manufactured in an analogous manner:

b) 4'-[(Allylmethylamino)methyl]-4-biphenylyl p-fluorophenyl ketone hydrochloride with a m.p. of 152°-153° C. Yield 74%.

c) 4'-[(Allylmethylamino)methyl]-4-biphenylyl 1-naphthyl ketone hydrochloride with a m.p. of 189°-190° C. Yield 44%.

d) 4'-[(Allylmethylamino)methyl]-4-biphenylyl 2-naphthyl ketone hydrochloride with a m.p. of 154° C. Yield 52%.

f) p-[[4'-[(Allylmethylamino)methyl]-4-biphenylyl]-carbonyl]benzonitrile hydrochloride with a m.p. of 91°-93° C. Yield 24%.

g) 4'-[[(Allylmethylamino)methyl]-4-biphenylyl p-bromophenyl ketone hydrochloride with a m.p. of 185° C. Yield 44%.

h) 4'-[[(Allylmethylamino)methyl]-4-biphenylyl p-iodophenyl ketone hydrochloride with a m.p. of 200° C. Yield 30%.

i) 4'-[[(Allylmethylamino)methyl]-4-biphenylyl 2-chloro-4-nitrophenyl ketone hydrochloride with a m.p. of 200° C. Yield 30%.

j) 2-Bromo-4-chlorophenyl 4'-[(allylmethylamino)-methyl]-4-biphenylyl ketone hydrochloride with a m.p. of 194°-195° C. Yield 64%.

EXAMPLE 6 a) A mixture of 10 g of 4-isopropenyl-biphenyl and 6.7 g of sodium azide in 50 mL of chloroform was cooled to −5° C. A solution of 20.6 g of trifluoroacetic acid in 50 mL of chloroform was added thereto in such a manner that the temperature remained below 0° C. The reaction mixture was then left to stand at room temperature overnight. The mixture was then treated with ice-water and 24 percent ammonium hydroxide and extracted three times with methylene chloride. The extracts were dried over magnesium sulphate and evaporated. The waxy residue was taken up in pentane, whereupon a small amount of insoluble material was filtered off. After evaporation of the filtrate there was obtained 10.9 g (89%) of 4-(1-azido-1-methyl)ethyl-biphenyl as a yellowish oil.

b) 10.9 g of 4-(1-azido-1-methyl)ethyl-biphenyl was dissolved in isopropanol and then heated to 70° C. The solution was then treated with small portions of moist Raney-nickel, whereby a strong evolution of nitrogen was observed. After completion of the addition, the reaction mixture was held at 70° C. for a further 0.5 hour and then filtered. The filtrate was partitioned between 2N hydrochloric acid and ethyl acetate. The mixture was again filtered in order to remove insoluble material and the organic phase was then discarded. The aqueous phase was made alkaline by the addition of sodium hydroxide and then extracted three times with ethyl acetate. The organic phase was dried over magnesium sulphate and evaporated. There was obtained 7.08 g (73%) of 4-(1-amino-1-methyl)ethylbiphenyl as a yellowish, crystalline solid.

c) 4.3 g of 4-(1-amino-1-methyl)ethylbiphenyl were dissolved in 40 mL of acetone and then treated with 2.7 mL of methyl iodide and 7.5 g of potassium carbonate. The mixture was heated to boiling under reflux for 6 hours and then evaporated. The residue was chromatographed on silica gel with methylene chloride/methanol 98:2 and then on aluminium oxide with hexane/ethyl acetate 98:2. There was obtained 2.06 g (28%) of 4-[1-(dimethyl-amino)-1-methylethyl]biphenyl.

d) 0.9 g of -[1-(dimethylamino)-1-methylethyl]biphenyl was dissolved in 9 mL of carbon disulphide and cooled to 0° C. The solution was treated with 1.1 g of aluminium chloride and then with 0.54 mL of benzoyl chloride. After completion of the addition the mixture was heated to 40° C. for 8 hours. The mixture was then treated with a further portion of 0.54 mL of benzoyl chloride and heated to 40° C. for a further 10 hours. The reaction mixture was then poured on to ice-water, made alkaline by the addition of sodium hydroxide and extracted with ethyl acetate. The organic phase was dried and evaporated, and the residue was chromatographed on aluminium oxide with ethyl acetate/hexane (1:4 and 1:1), there was obtained an impure residue. This was taken up in ether and treated with an ethereal solution of hydrogen chloride. The precipitated hydrochloride was filtered off and dried. There was obtained 0.42 g (29%) of 4'-[1-(dimethylamino)-1-methylethyl]-4-biphenylyl phenyl ketone hydrochloride as a yellowish solid with a m.p. of 241° C.

e) In an analogous manner there was obtained p-bromophenyl 4'-[1-dimethylamino)-1-methylethyl]-4-biphenylyl ketone hydrochloride with a m.p. of 237° C. Yield 21%.

EXAMPLE 7 a) A solution of the Grignard reagent prepared from 344 mg of magnesium and 2.27 g of 2-bromotoluene in 15 mL of tetrahydrofuran was added dropwise to a suspension of 2 g of (±)-1-dimethylamino-1-(4-bromophenyl)-ethane and 158 g of tetrakisphenylphosphine-palladium in 10 mL of tetrahydrofuran. The addition was effected at room temperature and under an argon atmosphere. After completion of the addition the mixture was heated to boiling for a further 5 hours and then evaporated under reduced pressure. The residue was then treated with 50 mL of ether and 50 mL of saturated ammonium chloride solution and the aqueous phase was separated. The aqueous phase was extracted twice with 50 mL of ether. The combined organic extracts were washed with saturated sodium chloride solution, dried over magnesium sulphate and evaporated. The residue was purified by chromatography on silica gel while eluting with methylene chloride/methanol 9:1. There was obtained 2.04 g (96%) of (±)-4'-[1-(dimethylamino)ethyl]-2-methylbiphenyl as a yellow oil.

b) A mixture of 4.76 g of (±)-4'-[1-(dimethylamino)ethyl]-2-methylbiphenyl, 2.94 g of hexamethylenetetramine and 30 mL of trifluoroacetic acid was heated to boiling under reflux for 5 days. The reaction mixture was then concentrated and treated with 100 mL of ice-water, whereupon it was stirred for 15 minutes, made basic with sodium carbonate and extracted with ether. After evaporation of the ethereal extracts and chromatography of the residue on silica gel with methylene chloride/methanol 9:1 as the elution agent there were obtained 2.8 g (52%) of (±)-4-[4'-(1-(dimethylamino)ethyl)phenyl]-2-methylbenzaldehyde as a yellow oil.

c) A solution of the Grignard reagent prepared from 0.94 g of bromobenzene and 146 mg of magnesium in 5 mL of tetrahydrofuran was added dropwise to a solution of 1.07 g of (±)-4-[4'-(1-(dimethylamino)ethyl)phenyl]-2-methylbenzaldehyde in 10 mL of tetrahydrofuran. The addition was effected at room temperature and under an argon atmosphere. The mixture was then stirred at room temperature for 6 hours and then hydrolyzed with 50 mL of saturated ammonium chloride solution. The mixture was extracted three times with 50 mL of ether each time, the extracts were dried over magnesium sulphate and evaporated. There were obtained 1.3 g of a material which was purified by chromatography on silica gel with methylene chloride/methanol 9:1 as the elution agent. There was obtained 1.1 g (80%) of (RS)-4'-[(RS-1-(dimethylamino)ethyl]-2-methyl-α-phenyl-4-biphenylmethanol as a colorless oil.

d) A solution of 406 mg of dimethyl sulphoxide in 2 mL of methylene chloride was added within 5 minutes to a solution of 327 mg of oxalyl chloride in 10 mL of methylene chloride at −70° C. The reaction mixture was stirred for 2 minutes, whereupon a solution of 810 mg of (RS)-4'-[(RS-1-(dimethylamino)ethyl]-2-methyl-α-phenyl-4-biphenylmethanol in 5 mL of methylene chloride was added thereto within 5 minutes. The reaction mixture was stirred for a further 15 minutes and then treated at −70° C. with 1.18 g of triethylamine. The reaction mixture was then left to warm to room temperature and was treated with 50 mL of a 5 percent aqueous solution of sodium carbonate. The aqueous phase was extracted twice with 50 mL of methylene chloride each time. The organic phases were combined, washed with 50 mL of saturated sodium chloride solution and dried over magnesium sulphate. After filtration and evaporation under reduced pressure there was obtained 780 mg of a material which was added to a hot solution of 263 mg of fumaric acid in 5 mL of ethanol. The precipitated fumarate was recrystallized from ethanol. There was obtained 810 mg (75%) of rac-4'-[1-(dimethylamino)ethyl]-2-methyl-4-biphenylyl phenyl ketone fumarate as a colorless solid with a m.p. of 166°–168° C.

EXAMPLE 8 a) In analogy to Example 7a):
From 4-iodo-N,N-dimethylbenzylamine and 3-bromotoluene there was obtained N,N,3'-trimethyl-4-biphenylmethanamine as a yellow liquid (b.p. 180°–185° C./20 Pa); and
from 4-iodo-N-allyl-N-methylbenzylamine and 3-bromotoluene there was obtained N-allyl-N,3'-dimethyl-4-biphenylmethanamine as a colorless liquid (b.p. 185°–190° C./20 Pa).

In analogy to Example 6d):
b) From N,N,3'-trimethyl-4-biphenylmethanamine and 2-methylbenzoyl chloride there was obtained 4'-[(dimethylamino)methyl]-3-methyl-4-biphenylyl o-tolyl ketone as a pale yellow liquid; yield 17%; mass spectrum: peaks: inter alia at m/e: 343 (M+, 42%), 299 (45%), 58 (100%);

c) from N,N,3'-trimethyl-4-biphenylmethanamine and 4-bromobenzoyl chloride there was obtained p-bromophenyl 4'-[(dimethylamino)methyl]-3-methyl-4-biphenylyl ketone as a yellowish solid with a m.p. of 108°–110° C.;

d) from N-allyl-N,3'-dimethyl-4-biphenylmethanamine and benzoyl chloride there was obtained 4'-[(allylmethylamino)-methyl]-3-methyl-4-biphenylyl phenyl ketone as a yellowish liquid; yield 25%; mass spectrum: peaks: inter alia at m/e: 355 (M+, 38%), 285 (100%), 84 (41%);

e) from N-allyl-N,3'-dimethyl-4-biphenylmethanamine and 4-bromobenzoyl chloride there was obtained 4'-[(allylmethylamino) methyl]-3-methyl-4-biphenylyl p-bromophenyl ketone and after treatment with hydrochloric acid in ether there was obtained the corresponding hydrochloride as a yellowish solid with a m.p. of 158°–160° C.; (yield 46%).

EXAMPLE 9 a) 6.15 g of pyridine was added dropwise at 0° C. under argon within 15 minutes to a solution of 5.43 g of 4'-methyl-biphenylcarboxylic acid chloride (Collect. Czech. Chem. Commun. 1978, 43, 257) and 2.53 g of N,O-dimethyl-hydroxylamine hydrochloride in 50 mL of methylene chloride. The reaction mixture was stirred at room temperature for 1 hour, then washed twice with 50 mL of a saturated sodium bicarbonate solution. The organic phase was dried over magnesium sulphate and concentrated. The residue was dried at room temperature and about 12 Pascual. There were obtained 6 g (98%) of N-methoxy-N-methyl-4'-methyl-4-biphenylcarboxamide as a colorless oil.

b) 4 g of N-methoxy-N-methyl-4'-methyl-4-biphenylcarboxamide, 3.34 g of N-bromosuccinimide and 0.02 g of azaisobutyronitrile in 50 mL of carbon tetrachloride were heated to boiling under reflux for 18 hours. The reaction mixture was diluted with 50 mL of methylene chloride and washed twice with 50 mL of water each time and once with 50 mL of saturated sodium chloride solution. The organic phases were dried over magnesium sulphate and concentrated. The residue was recrystallized from ethyl acetate. There was obtained 4.1 g (78%) of 4'-bromomethyl-N-methoxy-N-methyl-4-biphenylcarboxamide as a solid with a m.p. of 105°-106° C.

c) 1.95 g of 4'-bromomethyl-N-methoxy-N-methyl-4-biphenylcarboxamide was treated with 20 mL of a 33% solution of dimethylamine in ethanol, stirred at room temperature for 24 hours, the reaction mixture was evaporated, the residue was dissolved in 50 mL of ethyl acetate and washed with 50 mL of sodium hydroxide solution and with 50 mL of a saturated sodium chloride solution. The organic phases were dried over magnesium sulphate and evaporated. The crude product was chromatographed on 100 mL of silica gel with methylene chloride/methanol 9:1. There was obtained 1.16 g (52%) of 4'-[(dimethylamino)methyl]-N-methoxy-N-methyl-4-biphenylcarboxamide as a colorless solid with a m.p. of 42°-43° C.

d) A solution of the Grignard reagent prepared from 228 mg of magnesium and 1.42 g of n-pentyl bromide in 10 mL of tetrahydrofuran was added dropwise to a solution of 1.16 g of 4'-[(dimethylamino)methyl]-N-methoxy-N-methyl-4-biphenylcarboxamide in 10 mL of tetrahydrofuran at 0° C. under argon. After completion of the addition the mixture was stirred at room temperature for a further 5 hours and then evaporated under reduced pressure. The residue was treated with 50 mL of methylene chloride and 50 mL of saturated ammonium chloride solution and the aqueous phase was separated. The aqueous phase was extracted twice with 50 mL of methylene chloride. The combined organic extracts were washed with saturated sodium chloride solution, dried over magnesium sulphate and evaporated. The residue was purified by chromatography on silica gel while eluting with methylene chloride/methanol 95:5. 0.95 g of a colorless oil was obtained. The oil was taken up in ether and treated with an ethereal solution of hydrogen chloride. The precipitated hydrochloride was filtered off and dried. There was obtained 0.83 g (61%) of 4'-[(dimethylamino)-methyl]-4-biphenylyl pentyl ketone hydrochloride as a colorless solid with a m.p. of 243°-245° C.

EXAMPLE 10 a) In analogy to Example 9d), from 4'-[(dimethylamino)-methyl]-N-methoxy-N-methyl-4-biphenylcarboxamide and 5-bromomagnesium-2-methyl-2-pentene there was obtained 4'-[(dimethylamino)methyl]-4-biphenylyl 4-methyl-3-pentenyl ketone hydrochloride as a colorless solid (yield 48%) with a m.p. of 230°-232° C.

b) In analogy to Example 9d), from 4'-[(dimethylamino)-methyl]-N-methoxy-N-methyl-4-biphenylcarboxamide and 2-[(8-bromomagnesiumoctyl)oxy]tetrahydro-2H-pyran (J. Am. Chem. Soc. 1978, 100, 4878) there was obtained 4'-[(dimethylamino)methyl]-4-biphenylyl 8-hydroxyoctyl ketone hydrochloride as a colorless solid with a m.p. of 190°-191° C. Yield 34%.

EXAMPLE 11 a) In analogy to Example 9c), from 4'-bromomethyl-N-methoxy-N-methyl-4-biphenylcarboxamide and N-allyl-N-methylamine there was obtained 4'-[(allylmethylamino)methyl]-N-methoxy-N-methyl-4-biphenylcarboxamide as a colorless liquid (yield 65%).

$^1$N-NMR (CDCl$_3$): 2.25 (s, 3H), 3.06 (d, J=6.5 Hz, 2H), 3.38 (s, 3H), 3.54 (s,2H), 3.59 (s, 3H), 5.1-5.3 (m, 2H), 5.8-6.0 (m, 1H), 7.41 (d, J=8 Hz, 2H), 7.5-7.8 (m, 6H).

b) In analogy to Example 9d), from 4'-[(allylmethylamino)methyl]-N-methoxy-N-methyl-4-biphenylcarboxamide and n-pentylmagnesium bromide there was obtained 4'-[(allylmethylamino)methyl]-4-biphenylyl pentyl ketone hydrochloride as a colorless solid (yield 51%) with a m.p. of 146°-149° C.

c) In analogy to Example 10a), from 4'-[(allylmethylamino)methyl]-N-methoxy-N-methyl-4-biphenylcarboxamide and 5-bromomagnesium-2-methyl-2-pentene there was obtained 4'-[(allylmethylamino)methyl]-4-biphenylyl 4-methyl-3-pentenyl ketone as a pale yellowish oil. Yield 42%.

$^1$H-NMR (CDCl$_3$): 1.65, 1.70 (2s, 6H), 2.24 (s, 6H), 2.46 (q, J=7 Hz, 2H), 3.05 (t, J=7 Hz, 2H), 3.07 (d, J=6.5 Hz, 2H), 3.57 (s, 2H), 5.1-5.3 (m, 3H), 5.8-6.0 (m, 1H), 7.42 (d, J=8 Hz, 2H), 7.55 (d, J=8 Hz, 2H), 8.03 (d, J=8 Hz, 2H).

d) In analogy to Example 10b), from 4'-[(allylmethylamino)methyl]-N-methoxy-N-methyl-4-biphenylcarboxamide and 2-[(8-bromomagnesiumoctyl)oxy]tetrahydro-2H-pyran there was obtained 4'-[(allylmethylamino)methyl]-4-biphenylyl 8-hydroxyoctyl ketone fumarate as a colorless solid with a m.p. of 84°-85° C. Yield 46%.

EXAMPLE A

The compound 4'-[(allylmethylamino)methyl]-4-biphenylyl 4-bromophenyl ketone was used as follows as the active ingredient for the manufacture of tablets:

| Ingredients | mg/tablet |
| --- | --- |
| Active ingredient | 200 |
| Powd. lactose | 100 |
| Povidone K 30 (polyvinylpyrrolidone) | 15 |
| Na carboxymethyl starch | 10 |
| Talc | 3 |
| Magnesium stearate | 2 |
| Tablet weight | 330 |

The active ingredient and the powdered lactose were mixed intensively. The mixture obtained was then moistened with an aqueous solution of Povidone K 30 and kneaded, whereupon the resulting mass was granulated, dried and sieved. The granulate was mixed with the remaining ingredients and then pressed to tablets of suitable size.

I claim:

1. Compounds of the formula

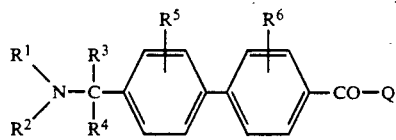

wherein $R^1$ and $R^2$ each independently are hydrogen, $C_{1-7}$-alkyl or $C_{2-7}$-alkenyl, or together are a straight chain $C_{2-4}$-alkylene; $R^3$ and $R^4$ each independently are hydrogen or $C_{1-7}$-alkyl; $R^5$ and $R^6$ each independently are hydrogen, halogen, trifluoromethyl, nitro, cyano, $C_{1-7}$-alkoxy or $C_{1-7}$-alkyl; and Q is an unsubstituted or substituted phenyl or naphthyl group, wherein the substituents are at least one of halogen, trifluoromethyl, cyano, nitro, $C_{1-7}$-alkyl, or $C_{1-7}$-alkoxy; $C_{2-10}$-alkenyl; or a hydroxy-substituted or unsubstituted $C_{1-10}$-alkyl group; or a pharmaceutically acceptable acid addition salt thereof.

2. A compound according to claim 1, wherein Q is an unsubstituted or substituted phenyl or naphthyl group, wherein the substituents are at least one of halogen, trifluoromethyl, cyano, nitro, $C_{1-7}$-alkyl or $C_{1-7}$-alkoxy.

3. A compound according to claim 1 wherein $R^1$ and $R^2$ each independently are $C_{1-4}$-alkyl or $C_{3-4}$-alkenyl.

4. A compound according to claim 2, wherein $R^1$ and $R^2$ each independently are $C_{1-4}$-alkyl or $C_{3-4}$-alkenyl.

5. A compound according to claim 1, wherein $R^5$ and $R^6$ each independently are hydrogen, halogen or $C_{1-4}$-alkyl.

6. A compound according to claim 1, wherein Q is (a) an unsubstituted, monosubstituted or disubstituted phenyl group wherein said substituents are selected from halogen, trifluoromethyl, nitro, cyano or $C_{1-4}$-alkyl; (b) a $C_{5-10}$-alkyl group; (c) a $C_{5-10}$-hydroxyalkyl group; or (d) a $C_{5-10}$-alkenyl group.

7. A compound of claim 1 which is selected from 4′-[1-(Dimethylamino)ethyl]-4-biphenylyl phenyl ketone;

4-bromophenyl 4′-[(dimethylamino)methyl]-4-biphenylyl ketone;
4′-[(dimethylamino)methyl]-4-biphenylyl 4-iodophenyl ketone;
4′-[1-(allylmethylamino)ethyl]-4-biphenylyl phenyl ketone;
4′-[1-(Allylmethylamino)methyl]-4-biphenylyl 4-bromophenyl ketone;
4′-[1-(allylmethylamino)methyl]-4-biphenylyl 4-iodophenyl ketone;
4′-[(Dimethylamino)methyl]-4-biphenylyl 4-methyl-3-pentenyl ketone,
4′-[(allylmethylamino)methyl]-4-biphenylyl 4-methyl-3-pentenyl ketone; and
4′-[(allylmethylamino)methyl]-4-biphenylyl 8-hydroxyoctyl ketone.

8. A pharmaceutical composition comprising a pharmaceutically effective amount of a compound of the formula

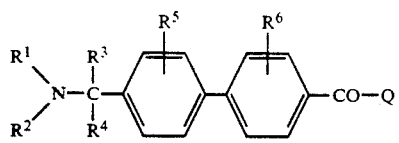

wherein $R^1$ and $R^2$ each independently are hydrogen, $C_{1-7}$-alkyl or $C_{2-7}$-alkenyl, or together are a straight chain $C_{2-4}$-alkylene; $R^3$ and $R^4$ each independently are hydrogen or $C_{1-7}$-alkyl; $R^5$ and $R^6$ each independently are hydrogen, halogen, trifluoromethyl, nitro, cyano, $C_{1-7}$-alkoxy or $C_{1-7}$-alkyl; and Q is an unsubstituted or substituted phenyl or naphthyl group, wherein the substituents are at least one of halogen, trifluoromethyl, cyano, nitro, $C_{1-7}$-alkyl, or $C_{1-7}$-alkoxy; $C_{2-10}$-alkenyl; or a hydroxy-substituted or unsubstituted $C_{1-10}$-alkyl group; or a pharmaceutically acceptable acid addition salt thereof.

9. A pharmaceutical composition comprising a effective amount of a compound of the formula

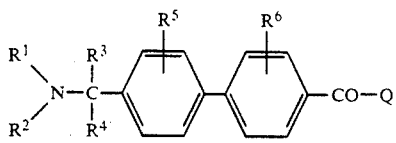

wherein $R^1$ and $R^2$ each independently are hydrogen, $C_{1-7}$-alkyl or $C_{2-7}$-alkenyl, or together are a straight chain $C_{2-4}$-alkylene; $R^3$ and $R^4$ each independently are hydrogen or $C_{1-7}$-alkyl; $R^5$ and $R^6$ each independently are hydrogen, halogen, trifluoromethyl, nitro, cyano, $C_{1-7}$-alkoxy or $C_{1-7}$-alkyl; and Q is an unsubstituted or substituted phenyl or naphthyl group, wherein the substituents are at least one of halogen, trifluoromethyl, cyano, nitro, $C_{1-7}$-alkyl, or $C_{1-7}$-alkoxy; $C_{2-10}$-alkenyl; or a hydroxy-substituted or unsubstituted $C_{1-10}$-alkyl group; or a pharmaceutically acceptable acid addition salt thereof and an antimycotically active compound which inhibits the biosynthesis of sterols.

10. A method of controlling or preventing topical or systemic fungal infections in a patient which comprises administering to said patient in need of such treatment an effective amount of a compound of the formula

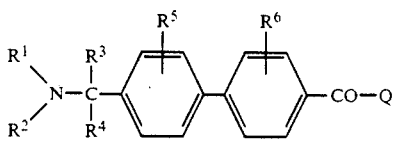

wherein $R^1$ and $R^2$ each independently are hydrogen, $C_{1-7}$-alkyl or $C_{2-7}$-alkenyl, or together are a straight chain $C_{2-4}$-alkylene; $R^3$ and $R^4$ each independently are hydrogen or $C_{1-7}$-alkyl; $R^5$ and $R^6$ each independently are hydrogen, halogen, trifluoromethyl, nitro, cyano, $C_{1-7}$-alkoxy or $C_{1-7}$-alkyl; and Q is an unsubstituted or substituted phenyl or naphthyl group, wherein the substituents are at least one of halogen, trifluoromethyl, cyano, nitro, $C_{1-7}$-alkyl, or $C_{1-7}$-alkoxy; $C_{2-10}$-alkenyl; or a hydroxy-substituted or unsubstituted $C_{1-10}$-alkyl group; or a pharmaceutically acceptable acid addition salt thereof.

11. A method of controlling or preventing topical or systemic fungal infections according to claim 10 which additionally comprises administering in combination with a compound of the formula

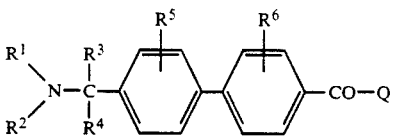

wherein $R^1$ and $R^2$ each independently are hydrogen, $C_{1-7}$-alkyl or $C_{2-7}$-alkenyl, or together are a straight chain $C_{2-4}$-alkylene; $R^3$ and $R^4$ each independently are hydrogen or $C_{1-7}$-alkyl; $R^5$ and $R^6$ each independently are hydrogen, halogen, trifluoromethyl, nitro, cyano, $C_{1-7}$-alkoxy or $C_{1-7}$-alkyl; and Q is an unsubstituted or substituted phenyl or naphthyl group, wherein the substituents are at least one of halogen, trifluoromethyl, cyano, nitro, $C_{1-7}$-alkyl, or $C_{1-7}$-alkoxy; $C_{2-10}$-alkenyl; or a hydroxy-substituted or unsubstituted $C_{1-10}$-alkyl group; or a pharmaceutically acceptable acid addition salt thereof
an effective amount of an antimycotically active compound which inhibits the biosynthesis of sterols.

* * * * *